United States Patent

Cichutek

(10) Patent No.: US 6,323,031 B1
(45) Date of Patent: Nov. 27, 2001

(54) LENTIVIRAL VECTORS DERIVED FROM SIVAGM, METHODS FOR THEIR PREPARATION AND THEIR USE FOR GENE TRANSFER INTO MAMMALIAN CELLS

(75) Inventor: Klaus Cichutek, Frankfurt am Main (DE)

(73) Assignee: Bundesrepublik Deutschland letztvertreten durch den Prasidenten des Paul-Elrich-Instituts Prof. Dr. R. Kruth (DE)

( * ) Notice: Subject to any disclaimer, the term of this patent is extended or adjusted under 35 U.S.C. 154(b) by 0 days.

(21) Appl. No.: 09/517,921

(22) Filed: Mar. 3, 2000

(30) Foreign Application Priority Data

Mar. 5, 1999 (DE) ............................... 199 09 769

(51) Int. Cl.[7] ........................... C12N 15/63; C12N 15/64; C12N 15/867; C12N 5/10

(52) U.S. Cl. ................... 435/456; 435/235.1; 435/320.1; 435/69.1; 435/455; 435/325; 435/366; 435/369

(58) Field of Search ............................. 435/235.1, 320.1, 435/69.1, 455, 456, 325, 366, 369; 424/93.1, 93.2, 93.6

(56) References Cited

PUBLICATIONS

Anderson, Nature, vol. 392, pp. 25–30, Apr. 1998.*
Verma et al., Nature, vol. 389, pp. 239–242, Sep. 1997.*
Kmiec, American Scientist, vol. 87, pp. 240–247, May 1999.*
Mountain, TIBTECH, vol. 18, pp. 119–128, Mar. 2000.*

* cited by examiner

*Primary Examiner*—David Guzo
(74) *Attorney, Agent, or Firm*—Fish & Richardson P.C.

(57) ABSTRACT

The preparation and use of novel lentiviral SiVagm-derived vectors for gene transfer and in particular a method of preparation of the lentiviral vectors containing capsid particles of the simian immunodeficiency virus SIVagm and envelope proteins of SIVagm and other retroviruses such as the human immunodeficiency viruses (HIV), other simian immunodeficiency viruses (SIV), other retroviruses such as the murine leukemia virus (MLV) or the "gibbon ape leukemia virus" (GaLV) or the porcine endogenous or exogenous retrovirus (PERV), the "vesicular stomatitis virus" (VSV-G) are described. The vectors and corresponding packaging cells may be employed for packaging and transfer of genes which are not packaged by other lentiviral, retroviral and other vectors or which show an inefficient gene transfer with other vector particles. These vectors may be used for gene transfer into selected cell types, specifically into proliferatively active and resting human cells.

7 Claims, 1 Drawing Sheet

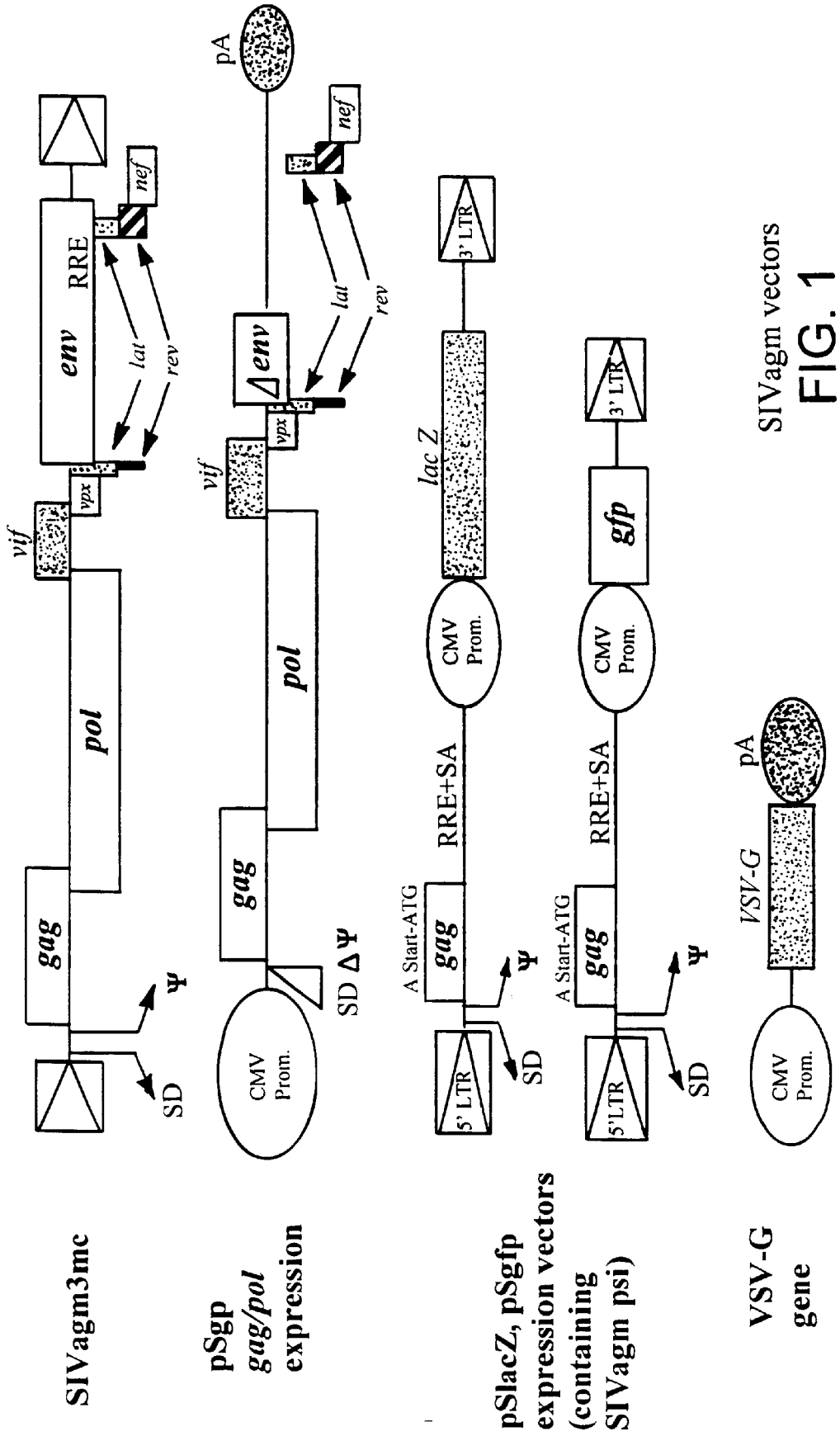

LENTIVIRAL VECTORS DERIVED FROM SIVAGM, METHODS FOR THEIR PREPARATION AND THEIR USE FOR GENE TRANSFER INTO MAMMALIAN CELLS

FIELD OF THE INVENTION

The object of the present invention are retroviral vectors (so-called lentiviral vectors) derived from SIVagm (AGM, African vervet monkey; Cercopithecus or Chlorocebus, respectively), methods for their preparation as well as their use for gene transfer into mammalian cells.

BACKGROUND OF THE INVENTION

The term "lentiviral vectors" or "SIVagm vectors" refers to infectious, but propagation-incompetent retroviruses capable of introducing genes into cells in the form of retroviral expression vectors (also called expression constructs or packaging-competent constructs). Lentiviruses refers to a group of retroviridae which following an infection of man, other primates, and mammals (e.g. sheep, cats) leads to a disease condition after a long incubation period. Gene transfer using retroviruses or lentiviruses, respectively, is also referred to as transduction. The gene transfer results in an integration of the expression vector into the cellular genome. Expression vectors include a packaging signal psi leading to incorporation of RNA of the expression vector into vector particles and to gene transfer. Therefore, "psi" refers to the retroviral packaging signal controlling efficient packaging of messenger RNA of the expression vector. Furthermore, the expression vector must be flanked by lentiviral LTR sequences ("long terminal repeats") in order to enable correct transcription of the RNA of the expression vector into DNA and subsequent integration of the expression vector gene into the chromosomal DNA of the cell. Lentiviral gene transfer is advantageous because (i) generally a copy of the desired gene is transduced into cells, (ii) usually, the gene is transferred without mutations or rearrangements, (iii) stable incorporation into the chromosome occurs, and (iv) genes can also be transferred into non-proliferating cells.

It has been known to use lentiviral vectors on the basis of the human immunodeficiency virus type 1 (HIV-1), type 2 (HIV-2), and the simian immunodeficiency virus of the rhesus monkey (*Macaca mulatta*) for the transfer of particular genes into mammalian cells and also specifically into human cells. A particular advantage of lentiviral vectors is their ability to transduce also resting or non-dividing cells, respectively. These vectors are propagation-incompetent and merely go through one cycle of replication. Three components are required for the preparation of such vectors. Within a packaging cell, a psi-negative gag/pol gene of the original lentivirus, a psi-negative env gene which may be derived from lentiviruses or other viruses, and a psi-positive and therefore packaging-competent expression construct usually also derived from a lentivirus. The expression vector enables packaging into the retroviral vector and transfer by the retrovirus to transduce a coding and translation-competent region of the desired gene product into the target cell. Following transduction of the plasmids containing the gag/pol gene, the env gene, and the expression vector gene by transfection of the three respective DNAs into a suitable mammalian cell, a packaging cell is generated which releases retroviral vector particles into the cell supernatant which exclusively contain the expression construct, however, lacking the psi-negative gag/pol and env genes so that these are not introduced into the target cells.

The tropism of lentiviral vectors, i.e. the selection of the mammalian cells into which they are able to transduce the expression construct is determined by the env gene in the packaging cell used and, thus, by the env gene products present in the vector particles. The env gene of retroviruses among which e.g. the murine leukemia virus (MLV), several lentiviruses such as HIV, SIV, or FIV ("feline immunodeficiency virus"), but also EIAV ("equine infectious anemia virus") or CIAV ("caprine infectious anemia virus") are used in the formation of lentiviral vector particles is translated into envelope proteins, the transmembrane protein (TM) and the surface envelope protein (SU) forming the outer envelope of the lentiviral vector. To date, mainly the env gene products of the amphotropic MLV, the GaLV ("gibbon ape leukemia virus") and the G protein of VSV ("vesicular stomatitis virus"; Burns et al., Proc. Natl. Acad. Sci. USA 90 (1993), 8033–8037) are used for gene transfer. They enable gene transfer into a wide variety of different mammalian cells and also in human cells. Particularly for selective gene transfer into human cells of a specific cell type, e.g. T cells or hematopoietic stem cells, the env gene products of the ecotropic, the amphotropic MLV or the spleen necrosis virus (SNV) are useful if they have been modified by introduction of domains of single chain antibodies (scFv, "single chain Fv") or other ligands for cell surface proteins such as for example cytokins or growth factors.

To improve the transduction of various genes, retroviral vectors have been proposed in which the gag/pol gene of different lentiviruses such as HIV-1, HIV-2, SIVmac, FIV, or EIAV was used instead of the gag/pol gene of oncoretroviruses such as MLV. Therefore, it is an object of the present invention to provide improved lentiviral vectors (retroviral virus particles).

This object has been achieved by the claimed invention.

SUMMARY OF THE INVENTION

The present invention features an SIVagm vector that includes a viral core derived from simian immunodeficiency virus (SIVagm) of the African vervet monkey (Chlorocebus, formerly *Cercopithecus aethiops*) and a viral envelope derived from SIVagm or another virus. The viral envelope can be derived from human immunodeficiency virus 1 or 2 (HIV-1 or HIV-2, respectively), simian immunodeficiency virus *Cercopithecus aethiops* (SIVagm), *Cercopithecus mitis* (SIVsyk), *Papio sphinx* (SIVmnd), *Cercocebus atys* (SIVsm), or *Macaca nemestrina* (SIVmne). The viral envelope used can include an envelope of the murine ecotropic or amphotropic leukemia virus (MLV), the avian spleen necrosis virus (SNV), the "gibbon ape leukemia virus" (GaLV), or the porcine endogenous or porcine exogenous retrovirus (PERV). A particular advantage of lentiviral vectors derived from SIVagm is that, when SIVagm envelope proteins are used, no (or only a low amount of) antibodies, particularly neutralizing antibodies, are formed against the vector. This enables many applications that are impossible with other lentiviral vectors. On the other hand, the vectors of the invention can also be used in the presence of anti-HIV antibodies that do not (or only slightly) inhibit gene transfer with SIVagm vectors having a homologous SIVagm envelope. A further distinctive feature of SIVagm vectors is that using their genes they may be packaged and transduced into mammalian cells which would inhibit the formation of the corresponding vector particles derived from HIV or other lentiviruses. For example, genes for antibodies directed against HIV-1 reverse transcriptase or integrase (anti-rt scFv and anti-int scFv genes) may be packaged and used for gene transfer by means of SIVagm vectors, while the use of HIV vectors for such gene transfers is inefficient or of very low efficiency.

In one embodiment of the present invention, any cell is transfected with a psi-negative expression gene for gag and pol genes of SIVagm. Furthermore, the cell may be transfected with an expression construct comprising a psi packaging signal and the genetic information to be transduced into the target cell. The expression construct may be derived from SIVagm, SIVmac, or HIV, however, it must enable packaging and transcription in association with the use of the enzymatic gene products of the pol gene and the capsid gene products of the gag gene of SIVagm. Then, the cell is transfected with another expression gene containing the genetic information for foreign or own envelope proteins. The cell line thus prepared produces lentiviral SIVagm-derived vectors containing the genetic information to be transduced.

In a preferred embodiment, the human cell line 293T is transfected simultaneously with the SIVagm gag/pol gene, the SIVagm env gene, and the packaging-competent expression vector pSgfp (see FIG. 1). Alternatively, plasmids are employed encoding the VSV G protein, the modified SNV env gene products, the MLV env gene products, the GaLV hybrid env gene products having lentiviral C termini. In this manner, a packaging cell line is generated releasing the lentiviral SIVagm-derived vectors of the present invention into the cell culture supernatant. These vectors contain capsid particles generated in the cell due to the expression of the SIVagm gagipol gene as well as packaging-competent lentiviral expression vector RNA carrying the genes to be transferred. In addition, the vector particles contain the SIVagm envelope proteins which are incorporated into the vector particles by intracellular expression of the SIVagm enm gene. Alternatively, the other env gene products mentioned may form the viral envelope. It has been demonstrated in detail that this resulted in the preparation of lentiviral vectors for gene transfer into proliferatively active or resting mammalian cells. The transduction by SIVagm vector particles having a SIVagm env envelope was not inhibited in the presence of antibodies against HIV. The surface envelope proteins of SIVagm and the other viruses mentioned have been detected on the surface of the gene transfer vectors prepared.

The present invention provides the following possibilities:

- transduction of genes into proliferatively active mammalian cells;
- transduction of genes into resting mammalian cells;
- transduction of genes into proliferatively active and resting CD4-positive mammalian cells;
- transduction of genes into proliferatively active and resting hematopoietic stem and precursor cells;
- transduction of genes into proliferatively active and resting neuronal cells;
- transduction of genes into other proliferatively active and resting human stem cells;
- transduction of genes into proliferatively active and resting human CD4-positive cells;
- transduction of genes into proliferatively active and resting human CD4-positive cells in the presence of anti-HIV antibodies;
- particularly for the development of gene therapy strategies for the treatment or prevention of HIV infection in humans by transducing HIV-inhibiting genes, e.g. antisense genes, RNA bait genes or transdominantly negative mutant genes of HIV or other lentiviruses into specific cells;
- in the context of gene therapy strategies for the treatment or prevention of HIV infection in humans for the development of vectors transducing HIV-inhibiting or other genes which may not be packaged and transduced by means of HIV-derived vectors into particular cells;
- particularly for the development of gene therapy strategies for introduction of genes into particular cells for the treatment or prevention of hereditary diseases such as ADA deficiency or other diseases which can be treated genetically in which the introduction into particular cells is advantageous such as for example T cell lymphomas, leukemias or other tumor diseases; and
- for a detailed study of the entry of lentiviruses into mammalian cells and the formation of lentiviral virions.

BRIEF FIGURE DESCRIPTION

The FIGURE is given to illustrate the present invention.

FIG. 1 schematically shows the structure of two expression vectors based on SIVagm, of the gag/pol and env genes based on SIVagm.

DETAILED DESCRIPTION

The term lentiviral vector as used herein means a replication-deficient SIVagM-derived retroviral virus particle having an envelope which is homologous or derived from other viruses and which is capable of transferring instead of retroviral MRNA a foreign introduced RNA of a gene, for example of a therapeutical gene or a fragment thereof, or of a reporter gene.

The term "therapeutical gene" as used herein means a nucleic acid sequence to be introduced into the target cell by means of the retroviral vector and comprises complete genes, fragments thereof, antisense nucleic acids and the like. The term SIV as used herein means viruses of the family of the simian immunodeficiency virus, e.g. according to *FIELDS*, Virology, "*Cercopithecus*" *aethiops* (SIVagm), recently renamed to Chlorocebus, *Macaca mulatta* (SIVmac), *Pan troglodytes* (SIVcpz), *Cercopithecus mitis* (SIVsyk), *Papio sphinx* (SIVmnd), *Cercocebus atys* (SIVsm) or *Macaca nemestrina* (SIVmne).

SUMMARY OF THE INVENTION

The following examples illustrate the present invention and should not be construed as limiting.

EXAMPLE 1

Preparation of SIVagm vectors having a homologous envelope

All of the genes or non-coding regions of SIVagm used herein are derived from the molecular clone SIVagm3mc (SWISS-PROT Accession number M3093 1). 293T cells were used for the preparation of vector particles. These were expanded in DMEM supplemented with 10% FCS and were seeded 24 hours prior to the start of transfection into 6-well plates (Nunc company, Wiesbaden) with $5\times10^5$ cells per cavity. As the transfection reagent, lipofectamin PLUS (Gibco company, Eggenstein) was used according to the manufacturer's instructions. For this purpose, 1 $\mu$g of plasmid DNA of each of the SIVagm3mc-derived gene constructs encoding gag/pol, env and the packaging-competent expression construct were transfected. After an incubation for four hours of the 293T cells with the DNA complexes described above the cells were washed and supplied with fresh medium. Two days after transfection the cell culture supernatants were harvested, and contaminating packaging cells were removed by filtration through a syringe filter (0.45 μm pore size).

EXAMPLE 2

Preparation of SIVagm vectors having an unmodified envelope of other retroviruses So-called pseudo type vectors were prepared according to the method described in example 1. However, heterologous envelope protein genes (env) of other viruses were used instead of homologous SIVagm envelopes. These may be derived from amphotrophic MLV (construct pHIT456, Soneoka et al., *Nucl. Acids Res.* 23:628–633, 1995), from "vesicular stomatitis virus" (pMD-g, Naldini et al., *Science* 272:263–267, 1996) or other viruses. The vector particles generated in this manner are composed of virus cores and an expression vector derived from SIVagm3 mc together with the heterologous envelope proteins used in each case.

EXAMPLE 3

Preparation of SIVagm vectors having a modified envelope

The preparation of SIVagm vectors having a modified envelope is also carried out as described above. However, in this case modified env genes are used which may be for example derived from SNV env. These include coding regions of antibodies or receptor ligands.

What is claimed is:

1. A propagation-incompetent SIVagm vector comprising a viral core and a viral envelope, wherein the viral core comprises a simian immunodeficiency virus (SIVagm) viral core of the African vervet monkey Chlorocebus.

2. The SIVagm vector of claim 1, wherein the viral envelope is the viral envelope of human immunodeficiency virus 1 or 2 (HIV-1 or HIV-2, respectively) or a simian immunodeficiency virus selected from the group consisting of *Cercopithecus aethipos* (SIVagm), *Macaca mulatta* (SIVmac), *Pan troglodytes* (SIVcps), *Cercopithecus mitis* (SIVsyk), *Papio sphinx* (SIVmnd), *Cercocebus atys* (SIVsm),and *Macaca nemestrina* (SVImne).

3. The SIVagm vector of claim 1, wherein the viral envelope protein is the viral envelope protein of the murine ecotropic or amphotropic leukemia virus (MLV), the avian spleen necrosis virus (SNV), the GaLV ("gibbon ape leukemia virus"), or the porcine endogenous or porcine exogenous retrovirus (PERV).

4. The SIVagm vector of claim 1, wherein the viral envelope further comprises a single chain antibody (scFv) or a ligand of a cell surface molecule.

5. A method for preparing a packaging cell that produces the SIVagm vector of claim 1, the method comprising transfecting a recipient cell with (a) a psi-negative expression construct comprising the gag and pol genes of SIVagm, (b) an expression construct comprising a psi packaging signal and the genetic information to be transduced into the target cell, and (c) an expression construct comprising the env gene of: (i) SIVagm, (ii) HIV-1, (iii) HIV-2, (iv) SIVmac, (v) SIVcpz, (vi) SIVsyk, (vii) SIVmnd, (viii) SIVsm, (ix) SIVmne, (x) MLV, (xi) SNV, (xii) GaLV, or (xiii) PERV.

6. A method for preparing a SIVagm vector, the method comprising transfecting a cell with (a) a psi-negative expression construct comprising the gag and pol genes of SIVagm, (b) an expression construct comprising a psi packaging signal and the genetic information to be transduced into the target cell, and (c) an expression construct comprising the env gene of: (i) SIVagm, (ii) HIV-1, (iii) HIV-2, (iv) SIVmac, (v) SIVcpz, (vi) SIVsxk, (vii) SIVmnd, (viii) SIVsm, (ix) SIVmne, (x) MLV, (xi) SNV, (xii) GaLV, or (xiii) PERV.

7. A packaging cell obtained by the method of claim 5.

* * * * *